United States Patent [19]

Gibson et al.

[11] Patent Number: 5,053,388

[45] Date of Patent: Oct. 1, 1991

[54] WOUND HEALING COMPOSITION AND METHOD

[75] Inventors: David Gibson, Irving, Calif.; Michael Lerner, Shawnee, Okla.; Robert Nordquist, Oklahoma City, Okla.; Cary Reich, Irvine, Calif.

[73] Assignees: Chiron Ophthalmics, Inc., Irvine, Calif.; Dean A. McGee Eye Inst., Oklahoma City, Okla.

[21] Appl. No.: 542,678

[22] Filed: Jun. 25, 1990

Related U.S. Application Data

[63] Continuation of Ser. No. 117,827, Nov. 9, 1987, abandoned.

[51] Int. Cl.$^5$ ............... A61K 37/02; A61K 31/21
[52] U.S. Cl. ............... 514/2; 514/8; 514/54; 514/508; 514/912; 514/913; 514/914; 514/915
[58] Field of Search ........... 514/2, 8, 54, 508, 912–915

[56] References Cited

U.S. PATENT DOCUMENTS

| | | | |
|---|---|---|---|
| 4,486,416 | 12/1984 | Soll et al. | 514/912 |
| 4,665,089 | 3/1987 | Siezen et al. | 514/912 |
| 4,703,108 | 10/1987 | Silver et al. | 514/801 |

*Primary Examiner*—Jacqueline Stone
*Attorney, Agent, or Firm*—Rothwell, Figg, Ernst & Kurz

[57] ABSTRACT

Improved healing of wounds, particularly wounds of the eye, such as keratorefractive surgical incisions, is obtained by coating the wound surfaces with a solution containing a protein crosslinking compound such as dimethyl pimelimidate dihydrochloride, followed by treatment with a composition containing an extracellular matrix material such as fibronectin, a biologically active fragment or an analog thereof.

20 Claims, 3 Drawing Sheets

FIG.1
FIG.3

WOUND HEALING COMPOSITION AND METHOD

This is a continuation of application Ser. No. 117,827, filed Nov. 9, 1987, now abandoned.

BACKGROUND OF THE INVENTION

This invention relates to compositions and methods for enhancing the quality of wound healing. In particular, the invention relates to the healing of corneal wounds. In one embodiment, the invention relates to methods and a composition for improving the results obtainable in keratorefractive surgeries, such as radial keratotomy, by altering the course of healing of the surgical incisions.

A considerable body of literature is devoted to methods for improving wound healing, both in terms of increasing rates of wound healing processes, such as scarring and contraction of healed tissue. Not only are those effects undesirable from a cosmetic point of view, but also, in the case of corneal wounds, they can interfere with visual function.

It is to be understood that the term "wound" as used herein includes surgical incisions as well as wounds caused by accidental trauma.

U.S. Pat. No. 4,444,787 describes the treatment of wounded ocular tissue by the topical application of collagen crosslinking inhibitors to the tissue. Application of the crosslinking inhibitor is said to reduce shrinkage of collagen fibers located in ocular tissue.

U.S. Pat. No. 3,438,378 describes a tissue adhesive comprising a mixture of soluble proteinaceous prepolymer, such as gelatin, a modifying agent in the form of a phenol derivative, and an aldehyde crosslinking agent. The tissue adhesive is applied to the surfaces to be bonded and crosslinking is effected.

A number of publications describe the use of tissue adhesives to bind wound surfaces following accidental corneal perforations or corneal surgery. These include: *Ophthalmic Surg.*, Vol. 15(1), pp. 55–57 (1984); *Aust. J. Ophthalmol.*, Vol. 11(2), pp. 113–118 (1983); *Ophthalmology*, Vol. 89(6), pp. 630–635 (1982); *Ophthalmic Surg.*, Vol. 13(6), pp. 475–477 (1982); *Ophthalmic Surg.*, Vol. 10(3), pp. 58–64 (1979); *J. Biomed. Mater. Res.*, Vol. 5(1), pp. 113–119 (1971); *Trans. Pac. Coast Ophthalmol. Soc.*, Vol. 50, pp. 121–135 (1969); *Trans. Am. Acad. Ophthalmol. Otolaryngol.*, Vol. 73(3), pp. 499–505 (1969). The most commonly employed adhesives for use in healing wounds of the eye are cyanoacrylate type adhesives.

Most of the foregoing publications describe methods and materials for binding together the surfaces of ocular tissue which has been penetrated accidentally or during surgery. In the cases described, the desired objective is to restore the wounded tissue as nearly as possible to its original configuration. In keratorefractive surgeries, however, incisions are made into the cornea for the specific purpose of permanently changing the geometry of the cornea. Restoration of the tissues to their original configuration, therefore, would tend to reverse the desired effects of the surgery.

Keratorefractive surgeries are intended to correct vision problems caused by defects in the geometry of the eye by surgically altering the corneal geometry. If successful, these techniques offer readily apparent advantages over conventional methods of vision correction, i.e., corrective lenses such as eyeglasses or contact lenses. Corrective lenses are often inconvenient or uncomfortable to wear and are subject to loss or breakage. Contact lenses present a risk of corneal infection and/or abrasion. These problems could be avoided if reliable keratorefractive surgical procedures could be developed that produced predictable, permanent vision correction.

Radial keratotomy is a keratorefractive surgical procedure which is employed to correct myopia caused by excessive corneal curvature. In this technique, a series of incisions is made in the cornea, usually penetrating about 90 to 95% of the thickness of the cornea. The incisions extend along lines which radiate outwardly from the corneal center. The number of incisions may vary from as few as four to as many as 16, with 8 to 12 being commonly employed. The incisions allow the cornea to relax and to flatten out somewhat, thereby reducing or eliminating nearsightedness. Similar procedures, in which corneal incisions are made in directions other than radial directions, have been employed to correct some astigmatisms.

While radial keratotomy and related keratorefractive surgeries have become fairly commonplace, the results achieved using presently available techniques are not highly predictable or controllable in any given patient. In particular, the degree of correction, measured in diopters, is not well controlled and may be more or less than is needed by the particular individual, so that the operation may have to be repeated or corrective lenses may still be needed. Furthermore, the healing process usually takes from 12 to 24 months, during which time some patients experience instability in visual acuity; that is, the cornea begins to reacquire some of the curvature lost as a result of the operation. Maximum flattening of the cornea usually occurs about 2 days after surgery, with a gradual increase in curvature occurring thereafter until the incisions have healed.

Some keratotomy patients have also encountered post-operative vision problems related to scarring. In some instances, scars at the healed incision sites cause light to be reflected within the eye, resulting in a perceived glare, particularly at night. Fluctuations in visual acuity throughout the day may also result.

The aforementioned problems encountered in keratorefractive surgery are related to the manner in which the corneal incisions heal. Yet, no efforts appear to have been made to improve the results obtained in keratorefractive surgery by significantly altering the course of healing of the surgical incisions.

A number of substances have been discussed in the literature in connection with corneal wound healing. Fibronectin, a plasma and extracellular matrix glycoprotein, has been applied as a topical wound-healing agent in the treatment of wounds or defects of the epithelial layer of the cornea (see Phan, T. M. et al., *ARVO 1985 Supplement to Investigative Ophthalmology & Visual Science*, Vol. 26, No. 3, p. 92 (1985); Nishida et al., *Arch. Ophthalmol.*, 101:1046–1048 (1983); Nishida et al., *Ophthalmology*, 92, 2, 213–216 (1985)). The appearance of fibronectin at the edges of stromal wounds in rabbit eyes was reported by Suda and coworkers (*Current Eye Research*, 1, 9, 553–556 (1982)). Dweck and coworkers have reported that type IIIc collagen and fibronectin are deposited at the site of stromal wounds in rabbits (*ARVO 1985 Supplement to Investigative Ophthalmology & Visual Science*, Vol. 26, No. 3, p. 92 (1985)).

SUMMARY OF THE INVENTION

This invention provides methods and compositions for enhancing the healing of wounds of the human or animal body. In particular, the methods and compositions of the invention can substantially enhance the results obtainable in keratorefractive surgery by altering the course of healing of surgical incisions of the cornea. Using the methods and compositions of the invention, substantial improvements can be obtained in the degree of refractive correction achieved in keratorefractive surgery. The degree of refractive correction obtained in a given patient is also more controllable and predictable than it is using prior art procedures. Further, the wound heals in a manner which minimizes scarring and the attendant risk of interference with visual function. The compositions of the invention can also be used as wound-healing agents and tissue adhesives in non-ophthalmological applications.

In accordance with the teachings of the invention, there is provided a method for enhancing the healing of wounds of the human or animal body. The method comprises applying to the surfaces of the wounds a composition comprising an effective amount of a protein crosslinking compound and an extra cellular matrix material, both in a pharmaceutically acceptable carrier therefore, or a composition of the extra cellular matrix material in a pharmaceutically acceptable carrier without the protein crosslinking compound. Examples of such compounds include aldehydes, e.g., formaldehyde and glutaraldehyde; di-imidates, e.g., dimethyl adipimidate and dimethyl pimelimidate; di-N-hydroxysuccinimide esters, e.g., bis (sulfosuccinimidyl) suberate and disuccinimidyl tartarate; photoreactive crosslinking agents, e.g., p-azidophenyl glyoxal and N-hydroxysuccinimidyl-4-azidobenzoimdate; heterobifunctional crosslinking agents, e.g., N-succinimidyl (4-iodoacetyl) aminobenzoate and succinimidyl 4-(N-maleimidomethyl)cyclohexane-1-carboxylate.

The method and composition of the invention can be employed specifically to enhance the healing of wounds of the human or animal cornea. In such case, the carrier material must be one which is ophthamologically acceptable. The compositions can be employed in the treatment of penetrating (full-thickness) wounds, wherein they promote faster healing with a stronger bond and reduction of scarring and tissue contraction. The compositions and methods of the invention can also reduce scarring and tissue contraction in dermal applications. In a preferred embodiment, the method of the invention is employed to enhance post-operative corneal healing following keratorefractive surgery. When the composition described above is applied to the walls of the keratorefractive incisions, permanent refractive correction is improved along with the aforementioned benefits of stronger bond formation and reduction in scarring and tissue contraction.

In one embodiment of the invention, keratorefractive incisions are treated with a wound-healing composition containing a protein crosslinking compound and with an extracellular matrix material such as fibronectin. Preferably, the protein crosslinking compound in solution with an ophthalmologically acceptable carrier material is first applied to the surfaces of the incision and a composition comprising an extracellular matrix material and an ophthalmologically acceptable carrier material is thereafter applied to the pretreated incision surfaces or used as a packing within the incision. Alternatively, the protein crosslinking compound and the extracellular matrix material can be applied in the form of a single composition comprising the protein crosslinking compound, an extracellular matrix material and an ophthalmologically acceptable carrier material.

BRIEF DESCRIPTION OF THE FIGURES

FIG. 1 is a photomicrograph of a cross-section of a primate cornea at the site of an incision 135 days after radial keratotomy in which the incision was not treated with any wound healing agent.

FIG. 3 is a photomicrograph of a cross-section of a primate cornea at the site of an incision 135 days after radial keratotomy in which the surfaces of the incision were treated with a composition containing dimethyl pimelimidate dihydrochloride.

In each of the photomicrographs of FIGS. 1–4, a dark line has been superimposed to show the boundaries of the original incision.

Figure 5:
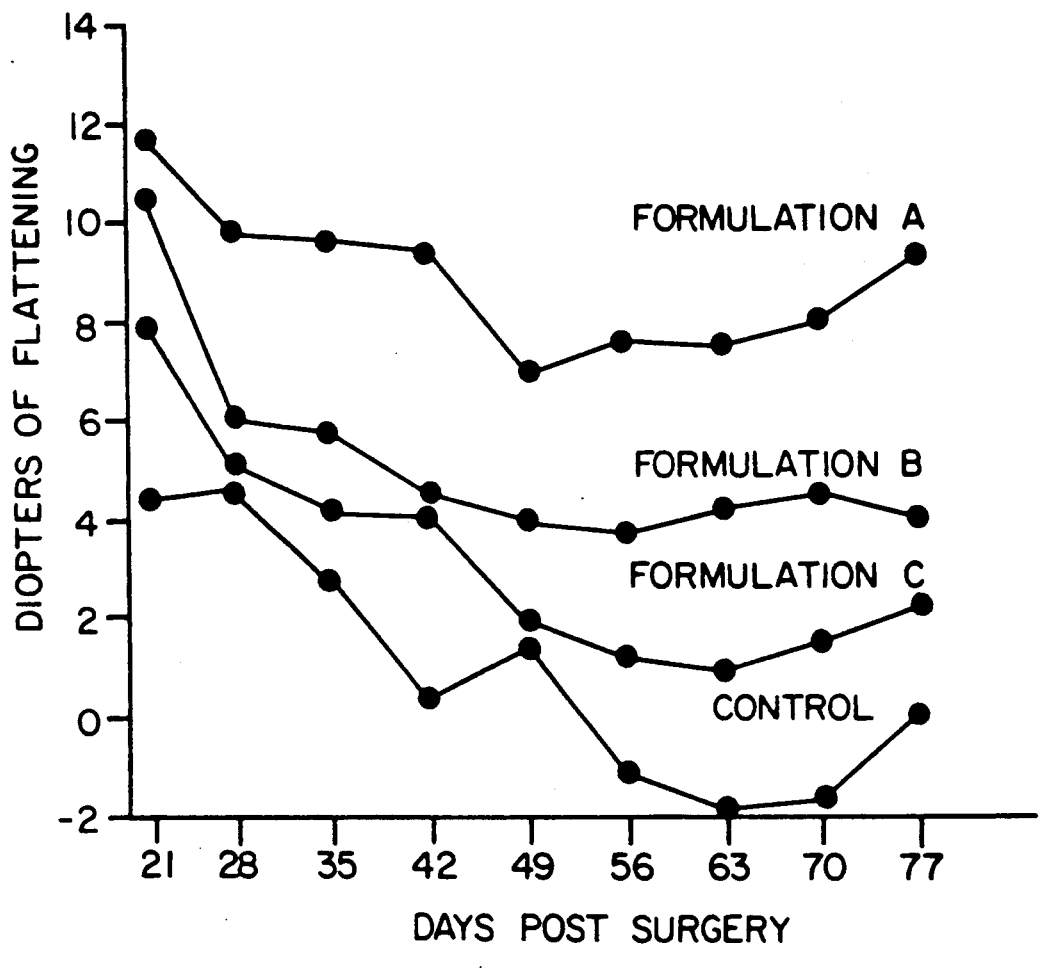

FIG. 5 is a graph which plots corneal flattening in radial keratotomies performed on primates as a function of post-surgical time for untreated controls and for corneas which had been treated with various wound-healing compositions.

DETAILED DESCRIPTION OF THE PREFERRED EMBODIMENTS

A wound-healing composition useful in the practice of the invention comprises a protein crosslinking compound, an extracellular matrix material and a pharmaceutically acceptable carrier therefore. The protein crosslinking compound can be any compound which is capable of covalently crosslinking protein molecules and which is pharmaceutically acceptable for the intended application. Examples of such compounds include aldehydes, e.g. formaldehyde and glutaraldehyde; di-imidates, e.g., dimethyl adipimidate and dimethyl pimelimidate; water soluble di-N-hydroxysuccinimide esters, e.g., bis (sulfosuccinimidyl) suberate and disuccinimidyl tartarate; photoreactive crosslinking agents, e.g. p-azidophenyl glyoxal, N-hydroxysuccinimidyl-4-azidobenzoate and methyl-4-azidobenzoate; and heterobifunctional crosslinking agents, e.g. N-succinimidyl (4-iodoacetyl)aminobenzoate and succinimidyl-4-(N-maleimidomethyl) cyclohexane-1-carboacylate. Other classes of compounds that are known to crosslink proteins and that are pharmaceutically acceptable can be employed.

Preferred protein crosslinking compounds for use in the present invention are those of the di-imidate ester class. These compounds can be defined by the formula:

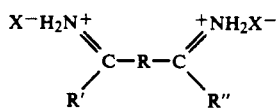 (I)

wherein
R is a divalent moiety such as
$-(CH_2)_n-$, $-S-S-$,

$-(CH_2)_n-S-S-(CH_2)_n-$ in which n is an integer of 1 or greater, preferably not more than about 20; R' and R'', which can be the same or different, are each alkoxy having from 1 to about 20 carbon atoms; and $X^-$ is an anionic counterion such as $Cl^-$ or $Br^-$. When R is $-(CH_2)n-S-S-(CH_2)_n-$, n is preferably 2.

One can mention, as exemplary of the preferred di-imidate compounds, dimethyl adipimidate.2HCl, dimethyl pimelimidate.2HCl and dimethyl-3,3'-dithiobispropionimidate.2HCl.

The most preferred compound is dimethyl pimelimidate dihydrochloride, which is the compound of the formula:

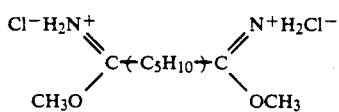 (II)

Dimethyl pimelimidate dihydrochloride has been used extensively as a fixative in histology applications.

The extracellular matrix materials (also referred to herein as "ECM materials") useful in the methods of the invention are materials which can be found in extracellular matrix structures laid down by cultured cells. (Hsieh, P. and Baum, J., *Invest. Ophth. & Vis. Sci.*, 26:457–463 (1985)). ECM materials include extracellular matrix proteins and extracellular ground substances. The former are generally high molecular weight (>150,000 daltons) fibrinous glycoproteins, which include fibronectin, collagens, vitronectin, elastin, laminin, actin and fibrinogen. The latter are polysaccharides, glycosylaminoglycans, which include chondroitin sulfate, heparin, keratan sulfate and hyaluronic acid or its sodium salt. It is to be understood that reference herein to ECM materials includes not only materials isolated from their natural sources, but also, materials produced synthetically, by means of expression in genetically engineered microorganisms or a combination of both. In the case of proteins or glycoproteins, such materials shall include biologically active fragments and analogs of such proteins or glycoproteins.

A preferred ECM material for use in the practice of the invention is fibronectin. Fibronectin is a glycoprotein (4–5% carbohydrate) having a molecular weight of about 220,000 daltons, which exists in the form of a 440,000-dalton dimer. Fibronectin exists in a plasma associated form and a cell associated form. It can conveniently be isolated from plasma by the procedure described by Nishida et al., *Jap. J. Ophth.*, Vol. 26, pp. 416–24 (1985). Fibronectin is also known by various other names, including cold-insoluble globulin, surface fibroblast antigen, cell surface protein, band 1, L1 band, band I, zeta-protein, major fibroblast glycoprotein, galactoprotein A, large external transformation sensitive protein (LETS), micro-fibrillar protein, cell attachment protein, cell adhesion factor, anti-gelatin factor, cell spreading factor and opsonic factor. For a review of the structure and activities of fibronectin, see Pearlstein, et al., *Mol. & Cell. Biochem.*, 29:103–125 (1980). Additionally, ECM proteins having a high degree of amino acid sequence homology with fibronectin, such as vitronectin (Suzuki, S., *J. Biol. Chem.*, 259:15307–15314 (1984) can be used in the wound healing compositions of the invention. Fragments of fibronectin, or analogs thereof, having the same type of cell-attachment activity as the full-length fibronectin molecule can also be used. Suitable fragments and methods of their preparation are disclosed in U.S. Pat. No. 4,589,881, issued to Piersbacher and Ruoslahti and U.S. Pat. No. 4,578,079, issued to Ruoslahti and Piersbacher, the disclosures of which are incorporated herein by reference. U.S. Pat. No. 4,589,881 discloses an 11.5 kDal, 108-amino acid fragment of fibronectin having cell attachment activity as well as a 30-amino acid subfragment which has cell attachment activity. U.S. Pat. No. 4,578,079 discloses fragments and analogs thereof having the formulae X-Arg-Gly-Asp-Thr-Y, X-Arg-Gly-Asp-Cys-Y and X-Arg-Gly-Asp-Ser-Y, wherein X is H or at least one amino acid residue and Y is COOH or at least one amino acid residue.

Typically, fibronectin is available in stabilized compositions which contain albumin and sugar as stabilizers, and buffering and osmolality controlling salts. The following lyophilized formulation exemplifies fibronectin compositions that may be used in the present invention:

| | |
|---|---|
| Fibronectin | 60.0 mg. |
| albumin | 30.0 mg. |
| sucrose | 150.4 mg. |
| NaCl | 25.4 mg. |
| $NaH_2PO_4.2H_2O$ | 3.3 mg. |
| $Na_2HPO_4.12H_2O$ | 3.5 mg. |

The fibronectin employed should be free of viral activity, such as hepatitis virus. Removal of hepatitis viral activity from fibronectin can be accomplished by the procedures set forth in U.S. Pat. No. 4,424,206 issued to Ohmura, et al., the disclosure of which is incorporated herein by reference.

The fibronectin can be employed, in the method of the invention, in the form of drops which are prepared by mixing the above-described formulation with saline to obtain the desired concentration of fibronectin.

Advantageously, there can also be applied to the wound surfaces, e.g., the surfaces of keratorefractive incisions, a growth factor such as epidermal growth factor. Growth factors are mitogenic proteins or polypeptides which promote cell proliferation. A number of growth factors are known. These include epidermal growth factor (EGF), transforming growth factors (TGF's) and nerve growth factor (NGF). Insulin, a polypeptide hormone, has mitogenic activity and can be used in conjunction with prostaglandin $F_{2\alpha}$, a non-peptide which has been shown to increase greatly the mitogenic activity of insulin (see Jimenez de Asua, L. et al., *Cold Spring Harbor Conf. Cell Proliferation*, Vol. 6, Sato, ed., Cold Spring Harbor Labs., New York [1979], at 403–424). Similar activation of insulin has been reported with fibroblast growth factor by Rudland, P. S. et al., *Proc. Natl. Acad. Sci., U.S.A.,* 76:1279-1293 (1974). Positive effects on cell growth have been demonstrated for platelet-derived growth factor or fibroblast-derived growth factor in combination with members of the insulin family such as somatomedins A and C (Stiles, C. D. et al., *Proc. Natl. Acad. Sci., U.S.A.,* 76:1279-1283 [1979]). Additionally, many new peptide growth factors have been isolated and characterized recently, as indicated in *Tissue Growth Factors,* R. Baserga, ed., Springer-Verlag pub., New York (1981).

As used herein "growth factor" includes mitogenically active fragments and analogs of natural or synthetic growth factors.

A preferred growth factor for use in the method of the invention is epidermal growth factor. EGF can be obtained from human tissues by the procedure described by Urdea et al., *PNAS (USA),* Vol. 80, p. 7461, by tissue extraction or by recombinant DNA techniques.

In accordance with the preferred method of the invention, a composition comprising the compound of formula I and an ophthalmologically acceptable carrier material is applied to the inner surfaces of keratorefractive incisions or lesions. The ophthalmologically acceptable carrier material is preferably a solution which is buffered to a pH at which the compound of formula I is capable of effecting crosslinking of protein molecules. Preferably, the solution is somewhat alkaline. In order to be ophthalmologically acceptable, the solution should not have a pH greater than about 8.5. Preferably, the compound of formula I is applied in a solution having a pH between about 7.5 and 8.5, most preferably about 7.8. Any suitable ophthalmologically acceptable carrier material can be employed. For example, a 0.3 m solution of NaOH in sterile water, having a pH between 13.0 and 14.0, can be admixed with 50 mg/ml of the compound of formula II to yield a solution having a pH between 7.5 and 8.5, which is useful in the method of the invention.

The composition can be applied to the incision or lesion surfaces by any suitable means which assures that the surfaces will be coated. For example, the composition can be injected into the incision through a needle or the incision can be manually held open and the composition can be used to flush the incision.

This treatment is then followed by application to the incision or lesion surfaces of a composition comprising an extracellular matrix material and an ophthalmologically acceptable carrier. This composition will also be referred to hereafter as a "Corneal Mortar composition." Preferably, this composition contains fibronectin as an extracellular matrix material. More preferably, it contains both fibronectin and chondroitin sulfate.

The Corneal Mortar composition generally has a higher viscosity than the composition containing the compound of formula I, due to the viscosity-increasing effect of the ECM materials. Advantageously, the composition has a thick, paste-like viscosity so that it can act as a packing material within the incisions. Since fibronectin and chondroitin sulfate are viscous materials, they are capable of imparting the desired viscosity to the Corneal Mortar compositions even at low concentrations. Fibronectin by itself begins to impart the desired viscosity when dissolved in saline solutions at concentrations of at least about 0.1% by weight. Preferably, fibronectin concentrations of about 0.5% by weight or higher most preferably about 2% by weight or higher are employed. Chondroitin sulfate by itself begins to impart the desired viscosity when dissolved in saline at levels as low as about 1%. While there is no strict upper limit on the viscosity of the composition, it should not be so viscous that it cannot be inserted into the wound by the physician.

Generally, the Corneal Mortar composition comprises from about 0.5% to 76% by weight ECM materials and from about 99.5% to 24% by weight of an ophthalmologically acceptable carrier material. Advantageously, the Corneal Mortar composition also contains a growth factor, such as EGF, in an amount which is effective to promote corneal cell growth at the incision site. Generally, the growth factor can be present in the corneal wound healing composition at a concentration from about 0.01 µg/ml to about 100 µg/ml, preferably from about 0.1 µg/ml to about 10 µg/ml, although there is no strict upper limit to the concentration of growth factor.

In one embodiment, the Corneal Mortar composition comprises fibronectin and an ophthalmologically compatible carrier material, the composition having a viscosity sufficiently high to retain the composition in the wound. The following formulation is exemplary of this embodiment:

| Ingredient | Amount* |
|---|---|
| Fibronectin | 0.5–40% |
| PBS** | 60–99.5% |

*Percentages based on total composition weight.
**Phosphate buffered saline. Other ophthalmologically acceptable carriers may also be substituted in the same amounts.

In another embodiment, the Corneal Mortar composition comprises fibronectin, chondroitin sulfate and an ophthalmologically compatible carrier material, the composition having a viscosity sufficiently high to retain the composition in the wound. The following formulation is exemplary of this embodiment:

| Ingredient | Amount |
|---|---|
| Fibronectin | 0.5–40% |
| Chondroitin sulfate | 0.5–75% |
| PBS | 24–99% |

In another embodiment of the invention, the Corneal Mortar composition comprises fibronectin, a growth factor and an ophthalmologically compatible carrier material, the composition having a sufficiently high viscosity to retain the composition in the wound. The following formulation is exemplary of this embodiment:

| Ingredient | Amount |
|---|---|
| Fibronectin | 0.5–40% |
| PBS | 60–99.5% |
| EGF | 0.01–100 g/ml |

In yet another embodiment, the Corneal Mortar composition comprises fibronectin, chondroitin sulfate, collagen and an ophthalmologically compatible carrier material, the composition having a sufficiently high viscosity to retain the composition in the wound. The following formulation is exemplary of this embodiment:

| Ingredient | Amount |
| --- | --- |
| Fibronectin | 0.5–40% |
| Chondroitin sulfate | 0.5–75% |
| Collagen | 0.5–50% |
| PBS | 24–98.5% |

In a preferred embodiment, the Corneal Mortar composition comprises fibronectin, chondroitin sulfate, a growth factor and an ophthalmologically acceptable carrier material, the composition having a sufficiently high viscosity to retain the composition in the wound. The following formulation is exemplary of this embodiment:

| Ingredient | Amount |
| --- | --- |
| Fibronectin | 0.5–40% |
| Chondroitin sulfate | 0.5–75% |
| PBS | 24–99% |
| EGF | 0.01–100 µg/ml |

The Corneal Mortar composition can be applied in an amount sufficient to coat the internal surfaces of the incision or it can be applied in an amount sufficient to pack all or a portion of the space between the surfaces of the incision. The Corneal Mortar composition can be placed into the surgical incision by the surgeon using any convenient means, such as by injection through a large-bore needle or by the use of any suitable trowel-like tool. The particular method which is best will depend largely on the viscosity of the Corneal Mortar composition.

If desired, a soft contact lens or a biological contact lens or shield which is permeable to gas and moisture, may be placed over the cornea post-operatively in order to allow moisture transmission while insuring that the Corneal Mortar composition remains in the incision. Alternatively, a hard contact lens, which forces the cornea to conform to the contact lens geometry, may be placed over the cornea in order to fix the desired shape of the cornea during the healing process.

The incisions which are made during keratotomy exhibit a V-shaped cross-section which penetrates through the epithelium (outer corneal layer), the basement membrane, Bowman's membrane and most of the thickness of the stroma (the thick structural layer of the cornea). In the normal course of healing of the incision, i.e., without using the methods of the invention, the inner surfaces of the incision tend to be drawn back together, starting from the bottom of the "V" in a zipper-like fashion. It is this drawing back together of the incision walls which causes the flattening effect of the keratotomy to become partially reversed as the incisions heal. While not wishing to be bound by any particular theory or mechanism of action, it is believed that the bifunctional compound of formula I reacts with free amine groups or other reactive groups on the collagen and other protein molecules along each internal surface of the incision. Consequently, the reactive sites along each incision wall, which would otherwise be free to form covalent bonds with similar reactive groups on the opposite wall, are effectively blocked by reaction with the bifunctional compound. There is thus created a "polishing" effect along the walls which prevents the original incision surfaces from drawing back together.

Application of Corneal Mortar composition also tends to prevent the original incision surfaces from drawing back together. Additionally, the Corneal Mortar composition provides a matrix for the deposition of wound-healing substances and for cell migration and growth. Thus, the wound-healing process is no longer constrained to take place at the surfaces of the incision, but rather, it can take place concurrently throughout the volume of space occupied by the Corneal Mortar composition. Placing the Corneal Mortar composition into the incision induces keratocytes to migrate into the space between the walls of the incision, where they grow and deposit wound-healing substances such as collagen.

A further advantage of using the Corneal Mortar composition relates to the organizational integrity of the healed tissue. Keratocytes, which are somewhat disc-shaped, are oriented in the plane of the "grain" in normal corneal stromal tissue. When wound healing proceeds without benefit of Corneal Mortar composition, keratocytes tend to be distributed within the healed area in a random orientation, which results in collagen being laid down from the edges of the keratocytes in a random orientation. This lack of orientation of keratocytes in control animals has been associated with increased scarring and cosmetically poor healing. On the other hand, when the Corneal Mortar composition is deposited in the wound, it provides a matrix which properly orients the keratocytes, so that collagen is laid down with the grain of the normal tissue.

Microscopic observation of keratorefractive incisions treated by the methods of the invention indicates not only that the walls of the originally V-shaped incision are prevented from drawing back together, but also that the original incision surfaces tend to move further apart toward the bottom of the incision during the healing process. This phenomenon is desirable in radial keratotomy, inasmuch as it tends to increase the degree of corneal flattening which is achieved. While this spreading of the incision surfaces toward the bottom of the incision has been observed using treatment with the compound of formula I alone, the effect is more pronounced and geometrically uniform using the compound of formula I in conjunction with the Corneal Mortar composition. In the latter case, the original incision surfaces, after healing, exhibit a cross-sectional configuration very similar in shape to a cross-sectional view of an Erlenmeyer flask. The degree and geometrical uniformity of incision spreading is optimal when the wound is treated with the composition containing the bifunctional compound of formula I followed by treatment with the Corneal Mortar composition.

Other ophthalmologically compatible substances which can be incorporated with the Corneal Mortar composition and/or the composition containing the bifunctional compound of formula I include substances which are known to promote wound healing or combat infection. For example, antibiotics, other antimicrobial agents, antiviral agents, antiinflammatory agents, antiprotease agents, hormones, vitamins, analgesics, chelating agents, mitogenic agents and the like can be employed in known effective amounts.

While it is preferred to treat the incision or lesion sequentially with the compound of formula I followed by treatment with the Corneal Mortar composition, the invention also contemplates treatment with a single composition containing both the compound of formula I and the components of the Corneal Mortar composition. In such an embodiment of the invention, the surfaces of the incision are treated with a composition comprising from about 0.5% to 30% by weight of a compound of formula I; from about 0.5% to 45% by weight of at least one ECM material; and from about 25% to 99% by weight of an ophthalmologically acceptable carrier material, the composition having a pH at which the compound of formula I is capable of effecting crosslinking of protein molecules. Preferably, the pH is from about 7.5 to 8.5 most preferably about 7.8.

Although the methods and compositions of the invention have been described in detail above with specific reference to their application in keratorefractive surgery, it is to be understood that the methods and compositions of the invention can be beneficially applied to other types of wounds. For example, they can be employed to enhance healing of penetrating wounds of the cornea caused by trauma or surgery or to enhance healing of dermal wounds. The compositions also have utility in promoting the healing of scleral wounds, such as incisions resulting from cataract surgery and intraocular lens implantation. The compositions of the invention promote more rapid wound healing and cause the wound to heal in a more orderly fashion. In dermal wounds, they can reduce scarring and contractile response.

The example which follows is intended to illustrate further the practice of the invention and is not to be construed as limiting the scope of the invention in any way.

EXAMPLE

Radial keratotomies were performed on a number of owl monkeys. Pre-operative treatment consisted of weight measurement, slit lamp examination, specular microscopy and corneascopic examination. A tatoo was placed at the center of the cornea.

To perform radial keratotamy, each animal was sedated with an intramuscular injection of ketaminexylazine and each eye was irrigated with preservative-free ophthalmic saline. For radial keratotomy, the optical zone was set by a 4-mm trephine at the central corneal tattoo. Using a ruby knife, an incision was made to 90% of the lowest corneal thickness based on pachometry readings taken prior to cutting. Radial keratotomy incisions were made at 12, 3, 6 and 9 o'clock and extended 7 mm.

Each cut was irrigated using a 27-g irrigation cannula with syringe containing preservative-free ophthalmic saline solution. The incision was dried with a cotton-tipped applicator or gauze.

Following radial keratotomy, one group of animals (minimum 2 eyes per treatment) was treated by applying a 1% solution of dimethyl pimelimidate dihydrochloride in ophthalmic saline to all the incision surfaces. The solution was applied to the incision surfaces, after drying them, using a triangular sponge. The animals were then treated with antibiotics and allowed to recover. A second group of animals was treated in a similar manner except that, immediately after application of the dimethyl pimelimidate dihydrochloride, the incisions were packed with a Corneal Mortar composition which had been prepared by mixing 50 mg fibronectin, 2.6 g chondroitin sulfate, 1.3 ml of 1% collagen and 30 $\mu$g of epidermal growth factor, all to a total volume of approximately 3.0 ml in saline solution. A third group of animals received the packing with Corneal Mortar composition, but not the treatment with dimethyl pimelimidate dihydrochloride. A fourth group did not receive either treatment following radial keratotomy.

Figures 2, 4:
FIG. 2 is a photomicrograph of a cross-section of a primate cornea at the site of an incision 135 days after radial keratotomy in which the surfaces of the incision were treated with a composition containing fibronectin.
FIG. 4 is a photomicrograph of a cross-section of a primate cornea at the site of an incision 135 days after radial keratotomy in which the surfaces of the incision were treated first with a composition containing dimethyl pimelimidate dihydrochloride and subsequently with a composition containing fibronectin, chondroitin sulfate and epidermal growth factor.

Corneal flattening was measured at 7-day intervals beginning at 21 days post-surgery and the average flattening for each experimental group was determined. At 135 days post-surgery, the animals were sacrificed. Cross-sections of the corneal incisions were prepared and examined under a light microscope. FIG. 1 is a photomicrograph of a cross-section of a corneal incision which was untreated following radial keratotomy. FIG. 2 is a photomicrograph of a cross-section of a corneal incision which received the Corneal Mortar composition following radial keratotomy. FIG. 3 is a photomicrograph of a cross-section of a corneal incision which was treated with dimethyl pimelimidate dihydrochloride. FIG. 4 is a photomicrograph of a cross-section of a corneal incision which was treated with dimethyl pimelimidate dihydrochloride followed by packing with the Corneal Mortar composition. The boundaries of the original incisions were determined by histological observation and superimposed as black lines on each photomicrograph.

Referring to FIG. 1, the original incision boundaries in the animals receiving no post-surgical treatment have drawn together and are nearly parallel. The space between the original incision boundaries is characterized by the deposition of unstructured collagen. FIG. 2 shows that the use of Corneal Mortar compositions to pack the incisions resulted in a widening of the space between the incision walls which was pronounced near the bottom of the incision. Additionally, the deposition of collagen between the original incision boundaries occurred in a much more orderly fashion, aligned with the plane of the normal stromal tissue. FIG. 3, in which dimethyl pimelimidate hydrochloride was used, shows a degree of widening between the original incision surfaces which gradually increases from the top to the bottom of the incision, such that the boundaries of the cross-section of the healed incision take on the geometric configuration of an Erlenmeyer flask. The deposition of collagen between the original incision surfaces is somewhat less ordered in FIG. 3 than in FIG. 2. FIG. 4 illustrates that optimal results, both in terms of geometry and organizational integrity, were achieved using both the dimethyl pimelimidate dihydrochloride pretreatment followed by Corneal Mortar packing. Maximal spreading of the original incision surfaces was achieved with a nearly pyrimidal geometry. This geometry is expected to result in maximal corneal flattening. Collagen bundles were deposited between the original incision surfaces in an orderly fashion similar to that seen in non-traumatized corneal stroma. This normalized restructuring of the corneal wound should produce significantly less light perturbation, thereby reducing or eliminating perceived glare.

Referring to FIG. 5, it can be seen that the degree of flattening which was predicted based on the histological studies was confirmed by corneascopic measurement. Throughout the course of healing, the cornea treated with both dimethyl pimelimidate dihydrochloride and Corneal Mortar composition (formulation A) exhibited the greatest degree of flattening, followed by dimethyl pimelimidate treatment alone (formulation B), Corneal Mortar composition treatment alone (formulation C), and no treatment (Control).

What is claimed is:

1. A method of enhancing the healing of corneal incision or lesion which comprises:

(a) coating the surfaces of the incision or lesion with a composition comprising a protein crosslinking compound and an ophthalmologically acceptable carrier material; and (b) applying to the incision or lesion a composition comprising an extracellular matrix material and an ophthalmologically acceptable carrier material.

2. A method as claimed in claim 1, wherein the protein crosslinking compound is a di-imidate compound of the formula

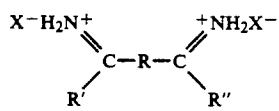

wherein
R is a moiety selected from the group consisting of

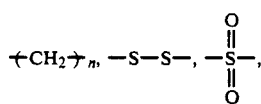

and $+CH_2+_nS-S+CH_2+_n$ in which n is an integer having a value of at least 1; R' and R", which can be the same or different, are each alkoxy having from 1 to 20 carbon atoms; and $X^-$ is an anionic counterion.

3. A method as claimed in claim 2, wherein $X^-$ is selected from $Cl^-$ and $Br^-$.

4. A method as claimed in claim 2, wherein R is alkylene having from 1 to 20 carbon atoms.

5. A method as claimed in claim 2, wherein R' and R" are each methoxy.

6. A method as claimed in claim 2, wherein R is $+CH_2+_nS-S+CH_2+_n$.

7. A method as claimed in claim 6, wherein n is 2.

8. A method as claimed in claim 1, wherein the protein crosslinking compound is dimethyl adipimidate dihydrochloride.

9. A method as claimed in claim 1, wherein the protein crosslinking compound is dimethyl-3,3'-dithiobispropionimidate dihydrochloride.

10. A method as claimed in claim 1, wherein the protein crosslinking compound is dimethyl pimelimidate dihydrochloride.

11. A method as claimed in claim 1, wherein the protein crosslinking compound is dimethyl suberimidate dihydrochloride.

12. A method as claimed in claim 1, wherein the extracellular matrix material is fibronectin, a biologically active fragment or an analog thereof.

13. A method as claimed in claim 1, wherein the extracellular matrix material contains fibronectin, a biologically active fragment or analog thereof and chondroitin sulfate.

14. A method as claimed in claim 13, wherein the composition which is applied to the incision or lesion in step (b) also contains a growth factor or a biologically active fragment or analog thereof.

15. A method as claimed in claim 14, wherein the growth factor is epidermal growth factor.

16. A method as claimed in claim 1, wherein the composition which is applied to the incision or lesion in step (b) comprises from about 0.1% to 40% by weight fibronectin, a biologically active fragment or analog thereof and from about 60% to 99.9% by weight of an ophthalmologically acceptable carrier material.

17. A method as claimed in claim 1, wherein the composition which is applied to the incision or lesion in step (b) comprises from about 0.5% to 40% by weight fibronectin, a biologically active fragment or analog thereof; from about 0.5% to 75% by weight of chondroitin sulfate; and from about 24% to 99% by weight of an ophthalmologically acceptable carrier material.

18. A method as claimed in claim 1, wherein the composition which is applied to the incision or lesion in step (b) comprises from about 0.5% to 40% by weight fibronectin, a biologically active fragment or an analog thereof; from about 60% to 99.5% by weight of an ophthalmologically acceptable carrier material; and from about 0.01 to 100 µg/ml of epidermal growth factor.

19. A method as claimed in claim 1, wherein the composition which is applied to the incision or lesion in step (b) comprises from about 0.5% to 40% by weight fibronectin, a biologically active fragment or analog thereof; from about 0.5% to 75% by weight chondroitin sulfate; from about 0.5% to 50% by weight collagen; and from about 24% to 98.5% by weight of an ophthalmologically acceptable carrier material.

20. A method as claimed in claim 1, wherein the composition which is applied to the incision or lesion in step (b) comprises from about 0.5% to 40% by weight fibronectin, a biologically active fragment or analog thereof; from about 0.5% to 75% by weight chondroitin sulfate; from about 24% to 99% by weight of an ophthalmologically acceptable carrier material; and from about 0.01 to 100 µg/ml of epidermal growth factor.

* * * * *